United States Patent
Xiao

(10) Patent No.: US 9,126,918 B2
(45) Date of Patent: Sep. 8, 2015

(54) PROCESS FOR PREPARING CYCLOHEXANOL AND CYCOHEXANONE FROM CYCLOHEXANE

(76) Inventor: Zaosheng Xiao, Suzhou (CN)

( * ) Notice: Subject to any disclaimer, the term of this patent is extended or adjusted under 35 U.S.C. 154(b) by 0 days.

(21) Appl. No.: 14/381,210

(22) PCT Filed: May 17, 2012

(86) PCT No.: PCT/CN2012/075627
§ 371 (c)(1),
(2), (4) Date: Aug. 26, 2014

(87) PCT Pub. No.: WO2013/143209
PCT Pub. Date: Oct. 3, 2013

(65) Prior Publication Data
US 2015/0105589 A1 Apr. 16, 2015

(30) Foreign Application Priority Data
Mar. 28, 2012 (CN) .......................... 2012 1 0085933

(51) Int. Cl.
| | |
|---|---|
| C07C 45/53 | (2006.01) |
| C07C 29/50 | (2006.01) |
| C07C 407/00 | (2006.01) |
| C07C 29/132 | (2006.01) |
| C07C 29/80 | (2006.01) |
| C07C 45/82 | (2006.01) |
| C07C 29/00 | (2006.01) |
| C07C 29/94 | (2006.01) |
| C07C 45/86 | (2006.01) |

(52) U.S. Cl.
CPC ............... *C07C 407/00* (2013.01); *C07C 29/00* (2013.01); *C07C 29/132* (2013.01); *C07C 29/50* (2013.01); *C07C 29/80* (2013.01); *C07C 29/94* (2013.01); *C07C 45/53* (2013.01); *C07C 45/82* (2013.01); *C07C 45/86* (2013.01); *C07C 2101/14* (2013.01)

(58) Field of Classification Search
CPC ................................ C07C 45/53; C07C 29/50
USPC .......................................... 568/354, 357, 836
See application file for complete search history.

(56) References Cited

U.S. PATENT DOCUMENTS 5,206,441 A     4/1993  Reimer

FOREIGN PATENT DOCUMENTS

| CN | 1035960 | 10/1989 |
| CN | 1621398 | 6/2005 |

*Primary Examiner* — Sikarl Witherspoon

(57) ABSTRACT

A process for preparing cyclohexanol and cyclohexanone from cyclohexane includes steps of: (1) non-catalyticly oxidizing cyclohexane with molecular oxygen to obtain an oxidized mixture liquid containing cyclohexyl hydroperoxide (CHHP) as a main product; (2) performing a homogenous catalytic decomposition with an oil-soluble transitional metal compound serving as a catalyst, and serving as a scale inhibitor by 1-hydroxy ethidene-1,1-diphosphonic acid (di)octyl ester, or a combination of 1-hydroxy ethidene-1,1-diphosphonic acid (di)octyl ester and phosphoric acid octyl ester, to decompose the CHHP in the oxidized mixture liquid into cyclohexanol and cyclohexanone; and (3) rectifying to obtain products of the cyclohexanol and the cyclohexanone.

6 Claims, No Drawings

PROCESS FOR PREPARING CYCLOHEXANOL AND CYCOHEXANONE FROM CYCLOHEXANE

CROSS REFERENCE OF RELATED APPLICATION

This is a U.S. National Stage under 35 U.S.C. 371 of the International Application PCT/CN2012/075627, filed May 17, 2012, which claims priority under 35 U.S.C. 119(a-d) to CN 201210085933.6, filed Mar. 28, 2012.

BACKGROUND OF THE PRESENT INVENTION

1. Field of Invention

The present invention relates to a process for preparing cyclohexanol and cyclohexanone from cyclohexane, and more particularly to an improvement in a scale inhibitor of a cyclohexyl hydroperoxide (CHHP) homogeneous catalytic decomposition in the process.

2. Description of Related Arts

The conventional process for the preparation of cyclohexanol and cyclohexanone comprises: non-catalyticly oxidizing cyclohexane with molecular oxygen to obtain an oxidized mixture containing cyclohexyl hydroperoxide (CHHP) as a main product; decomposing the CHHP to obtain cyclohexanol and cyclohexanone; and rectifying to obtain products of the cyclohexanol and the cyclohexanone. Internationally, the art of decomposing the CHHP to obtain the cyclohexanol and the cyclohexanone comprises two manners: the homogeneous catalytic decomposition by bis(tert-butyl)chromate, disclosed by French Rhodia Company; and, the non-homogeneous catalytic decomposition by cobalt acetate in the alkaline aqueous solution of sodium hydroxide, disclosed by Dutch DSM.

The homogeneous catalytic decomposition of CHHP by the bis(tert-butyl)chromate has two serious defects. Firstly, during decomposing, the scale formation, mainly the chromium adipate, blocks equipments and pipelines. Disclosed by Rhodia, the phosphoric acid octyl ester is used as the scale inhibitor, wherein the weight ratio of the phosphoric acid octyl ester to the catalyst transitional metal ions is 14:1, which fails to completely solve the scale formation. The continuous production cycle only lasts for four months; washing and descaling after stalling the production device are executed three times per year, which consumes a large amount of the phosphoric acid octyl ester as the scale inhibitor, more than ten times of the weight of the catalyst transitional metal ions. Secondly, the conversion rate is low, wherein the molar conversion rate is only around 92%; and around 5% of the CHHP still remains in the decomposed materials. The remaining CHHP is decomposed under the conditions of a high concentration of cyclohexanol and cyclohexanone, high acidity and a high temperature inside the cyclohexane recycling towers and the cyclohexanol and cyclohexanone product towers, so as to mainly produce acid compounds, like adipic acid, and ester compounds, mainly caprolactone; to speed up the condensation reaction of free radicals of the cyclohexanol and the cyclohexanone, and the esterification reaction of cyclohexanol; and to generate the high-boiling-point substances, reduce the yield and results in the total molar yield of only 80%.

The non-homogeneous catalytic decomposition by cobalt acetate in the alkaline aqueous solution of sodium hydroxide also has two defects. Firstly, the alkaline decomposition normally compromises with the big secondary reactions, and induces a low decomposition molar yield of only 84%. Secondly, it is difficult to completely separate the cyclohexane oil phase containing cyclohexanol and cyclohexanone from the alkaline aqueous phase containing the alkaline waste. The oil phase always contains a certain amount of the waste alkaline aqueous phase, in such a manner that the scales of the waste alkaline are always formed in the rectification towers subsequently, which blocks the rectification towers and the reboilers thereof, and results in the continuous production cycle of only six months and the total molar yield of only 80%.

Conventionally, the worldwide companies respectively adopt one of the above two manners to accomplish decomposing the CHHP at one step. The Chinese patents ZL9411039.9 and ZL98112730.4, filed by the inventor of this application, disclose the two-step alkaline decomposition art. At the first step thereof, the alkalinity is lowered; the recycling amount of the alkaline aqueous phase is increased; the static mixer and the plug flow tower-typed decomposing reactor are used. Industrial application results indicate that, the total molar yield of the device thereof really increases, but the separation of the cyclohexane oil phase from the waste alkaline aqueous phase becomes more difficult. The several sets of industrial production devices of the whole two-step alkaline decomposition art have a molar total yield of around 82%.

SUMMARY OF THE PRESENT INVENTION

An object of the present invention is to provide a process for preparing cyclohexanol and cyclohexanone from cyclohexane, the process having a long continuous production cycle, a small consumption of a scale inhibitor and a high total yield, and improving a catalytic activity in a decomposition reaction of a homogenous catalyst.

Accordingly, in order to accomplish the above objects, the present invention adopts the following technical solutions.

A process for preparing cyclohexanol and cyclohexanone from cyclohexane comprises steps of:

(1) non-catalyticly oxidizing cyclohexane with molecular oxygen to obtain an oxidized mixture liquid containing cyclohexyl hydroperoxide (CHHP) as a main product;

(2) performing a homogenous catalytic decomposition with an oil-soluble transitional metal compound which serves as a catalyst to decompose the CHHP into cyclohexanol and cyclohexanone; and (3) rectifying to obtain products of the cyclohexanol and the cyclohexanone.

The step (2) further comprises: serving as a scale inhibitor by 1-hydroxy ethidene-1,1-diphosphonic acid (di)octyl ester, or a combination of 1-hydroxy ethidene-1,1-diphosphonic acid (di)octyl ester and phosphoric acid octyl ester. For the step of "serving, by 1-hydroxy ethidene-1,1-diphosphonic acid (di)octyl ester, as the scale inhibitor", a weight ratio of 1-hydroxy ethidene-1,1-diphosphonic acid (di)octyl ester to transitional metal ions is 1:0.8~1.2. For the step of "serving, by the combination of 1-hydroxy ethidene-1,1-diphosphonic acid (di)octyl ester and the phosphoric acid octyl ester, as the scale inhibitor", an amount of the scale inhibitor is calculated according to an equation that a descaling capacity of 20 tons of phosphoric acid octyl ester is equal to the descaling capacity of 1 ton of 1-hydroxy ethidene-1,1-diphosphonic acid (di)octyl ester.

Preferably, an amount of the scale inhibitor, 1-hydroxy ethidene-1,1-diphosphonic acid (di)octyl ester: the weight ratio of 1-hydroxy ethidene-1,1-diphosphonic acid (di)octyl ester to the transitional metal ions in the catalyst, namely the oil-soluble transitional metal compound, is 1:0.9~1.1.

The 1-hydroxy ethidene-1,1-diphosphonic acid (di)octyl ester has a molecular formula of:

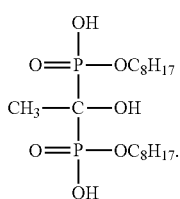

Further preferably, the weight ratio of 1-hydroxy ethidene-1,1-diphosphonic acid (di)octyl ester to the transitional metal ions in the catalyst, namely the oil-soluble transitional metal compound, is 1:1.

Preferably, when the scale inhibitor is served by the combination of 1 ton of 1-hydroxy ethidene-1,1-diphosphonic acid (di)octyl ester and 20 tons of phosphoric acid octyl ester, the weight ratio of the amount of the scale inhibitor to the transitional metal ions of the catalyst is 7.4:1.

The oil-soluble transitional metal compound is one member selected from a group consisting of cobalt naphthenate, chromium naphthenate, cobalt octoate, chromium octoate and bis(tert-butyl)chromate. The phosphoric acid octyl ester is a combination of 70% (weight percentage) of mono(2-ethylhexyl)phosphate and 30% of di(2-ethylhexyl)phosphate.

According to researches about CHHP decomposition mechanism and scaling mechanism conducted by the inventor, a free radical polymerization reaction and an aldol condensation reaction are simultaneously performed during the process of the CHHP homogeneous catalytic decomposition, so as to generate acid polymers having a core of an organic acid salt, typically represented by a metal adipate, in a decomposition reactor. The polymers having metal ions are un-soluble in a cyclohexane phase and have a polarity. Moisture within a system of the decomposition accelerates a gathering of the acid polymers, so as to form viscous scales which attach to inner walls of equipments and pipelines of the system. With time passed by, the viscous acid polymers become dehydrated and harden, so as to block the equipments and the pipelines and stop the continuous production cycle. According to the inventor's research, 1-hydroxy ethidene-1,1-diphosphonic acid (di)octyl ester shows a strong chelate property to the metal ions, and has a complexometric stability constant $10^3 \sim 10^5$ times larger than the common phosphoric acid octyl ester and phosphorous acid octyl ester. 1 mol of 1-hydroxy ethidene-1,1-diphosphonic acid (di)octyl ester at a relatively strong acidity is able to prevent the transitional metal ions of 6 mol of the catalyst from scaling and depositing; however, only at a slightly acidity is 3 mol of the phosphoric acid octyl ester able to prevent the transitional metal ions of 1 mol of the catalyst from scaling and depositing. Thus, according to the present invention, a first function of 1-hydroxy ethidene-1,1-diphosphonic acid (di)octyl ester is for complexation, namely 1-hydroxy ethidene-1,1-diphosphonic acid (di)octyl ester chelates with the metal ions of the catalyst after being added to the CHHP cyclohexane-phased decomposition system. Thereby, the metal ions generate metal chelates of 1-hydroxy ethidene-1,1-diphosphonic acid (di)octyl ester which are soluble in the cyclohexane phase, which greatly reduces the deposit of the metal ions of the catalyst. A second function of 1-hydroxy ethidene-1,1-diphosphonic acid (di)octyl ester is for painting walls. Because of the complexation between a polar group of 1-hydroxy ethidene-1,1-diphosphonic acid (di)octyl ester, i.e., a phosphoric hydroxyl group, and metal walls of the devices and pipelines, a layer of stable molecular 1-hydroxy ethidene-1,1-diphosphonic acid (di)octyl ester film is formed on the metal walls, which turns the polar metal walls into non-polar oily walls and thus disables the polar scales to attach onto the walls. A third function of 1-hydroxy ethidene-1,1-diphosphonic acid (di)octyl ester is for lattice dislocation. That is to say, 1-hydroxy ethidene-1,1-diphosphonic acid (di)octyl ester reacts with the metal catalyst ions of the adipate scales to dislocate a lattice of the scales, and prevents the scales from enlarging, in such a manner that the scales generate small particles which are soluble in the cyclohexane phase, wherein the small particles are unable to block the devices and pipelines and even remain a certain catalytic activity. The phosphoric acid octyl ester has no chelate property, but has a complexation ability far weaker than 1-hydroxy ethidene-1,1-diphosphonic acid (di)octyl ester, even weaker than the adipic acid at a high concentration. When the concentration of the adipic acid in the decomposition material becomes high, most of the metal ions have reacted with the adipic acid into the depositing adipate which is un-soluble in the cyclohexane phase, so as to form the scales having the core of the adipate. Therefore, before serving as the scale inhibitor by the phosphoric acid octyl ester, the cyclohexane oxidized liquid requires washing, until a majority of the adipic acid and low carbonate is removed by water washing; moreover, a large amount of phosphoric acid octyl ester is necessary, wherein a molar ratio of the phosphoric acid octyl ester to the metal ions is over 3:1, and a weight ratio thereof is over 11:1.

Conventionally, in the nylon factory of Liaoyang Petroleum & Chemical Fiber Company of China National Petroleum Corporation, the scale inhibitor was the phosphoric acid octyl ester comprising 70% of mono(2-ethylhexyl)phosphate and 30% of di(2-ethylhexyl)phosphate; 115 tons of the scale inhibitor, and 10 tons of chromium in the catalyst were consumed per year, namely the weight ratio of the phosphoric acid octyl ester to the chromium metal ions was 11.5:1. Based on such a ratio, each continuous production cycle lasted for four months and stopped three times per year; a decomposition reactor, all cyclohexane recycling towers and correspondent pipelines were washed with a NaOH aqueous solution each time, which caused much pollution water and polluted the environment. Herein it is worth to mention that, tris(2-ethylhexyl)phosphate has no complexation property; di(2-ethylhexyl)phosphate has a complexation property hardly competitive with a binary organic acid, such as the adipic acid; and mono(2-ethylhexyl)phosphate has a strong complexation property, and is able to suppress the scale formation having the core of the adipate to some extent. However, mono(2-ethylhexyl)phosphate and water generated by the CHHP decomposition are liable to hydrolyze to generate phosphoric acid; besides, the product of the phosphoric acid octyl ester originally contains a certain amount of phosphoric acid. The phosphoric acid has a stronger acidity than the phosphoric acid octyl ester, and is more liable to react with the transitional metal ions to generate the hard scales of the depositing phosphate. In other words, a concentration product of salts formed by the phosphate and the transitional metal ions of the catalyst is small. The above is the reason why the decomposition reactor discharging pump had to stall and required washing every 15 days, and also the reason why the CHHP homogeneous decomposition system and the cyclohexane recycling towers must be washed with alkaline water every four months.

According to the above scaling mechanism, in a first industrial experiment, the inventor cuts off half of the amount of the phosphoric acid octyl ester without changing other parameters, only uses less than 60 tons of the phosphoric acid octyl ester, and replaces the cut half with 1-hydroxy ethidene-1,1- diphosphonic acid (di)octyl ester, only 3 tons per year. In other words, 1 ton of 1-hydroxy ethidene-1,1-diphosphonic acid (di)octyl ester is used to replace 20 tons of the phosphoric acid octyl ester. The first industrial experiment shows that the continuous production cycle is elongated to be more than six months, and a conversion rate and a yield of the CHHP decomposition are increased by 1%; and especially that the decomposition discharging pump no longer forms scales and requires washing. A production capacity of the cyclohexanol and cyclohexanone device enlarges from 42,880 ton/year to more than 55 thousands ton/year; a consumption of the scale inhibitor, 1-hydroxy ethidene-1,1-diphosphonic acid (di)octyl ester, is around 4 ton/year; and a consumption of the phosphoric acid octyl ester is 70 ton/year. In a second industrial experiment, the inventor replaces all of the phosphoric acid octyl ester with 1-hydroxy ethidene-1,1-diphosphonic acid (di)octyl ester. The consumption of 1-hydroxy ethidene-1,1-diphosphonic acid (di)octyl ester is 8~10 tons. The scale formation of the CHHP homogeneous catalytic decomposition by bis(tert-butyl)chromate is completely solved.

According to the conventional arts, when the scale inhibitor comprises the phosphoric acid octyl ester, before entering the step of the homogeneous catalytic decomposition, the cyclohexane oxidized liquid must be condensed and rectified to separate out approximately 50% of cyclohexane, and then be extracted and rinsed to remove strongly acid by-products, such as the adipic acid, the low carbonate and caproate peroxide; otherwise, the production cycle only lasts for 1~2 months.

According to the present invention, all of the phosphoric acid octyl ester are replaced with 1-hydroxy ethidene-1,1-diphosphonic acid (di)octyl ester as the scale inhibitor. The oxidized liquid is able to enter the homogenous catalytic decomposition with or without condensing and rinsing. The production cycle of the cyclohexane oxidized liquid homogenous catalytic decomposition is able to last for more than six months without the scale formation, enhance the catalyst activity and significantly improve the total yield of the device.

DETAILED DESCRIPTION OF THE PREFERRED EMBODIMENT

These and other objectives, features, and advantages of the present invention will become apparent from the following detailed description, the accompanying drawings, and the appended claims.

Comparison Example

Phosphoric acid octyl ester is used as a scale inhibitor. 142.178 ton/hour of a cyclohexane oxidized mixture liquid flow out of an oxidation reactor, comprising 134.038 ton/hour of cyclohexane, 1.164 ton/hour of cyclohexanol, 0.534 ton/hour of cyclohexanone, 4.339 ton/hour of peroxide (CHHP), 1.698 ton/hour of acid and 0.405 ton/hour of impurity. Then the cyclohexane oxidized mixture liquid is processed with flash vaporization, condensation and rectification, wherein 76.51 ton/hour of the cyclohexane are evaporated through a tower top; 15.136 ton/hour of a reflux liquid are applied; 61.374 ton/hour of the rest return to the oxidation reactor after rinsing, in such a manner that a tower bottom obtains 80.804 ton/hour of a condensation liquid of the cyclohexane oxidized mixture. The obtained condensation liquid is rinsed with deionized water in a rinsing tower, so as to remove most of organic acid therein. 83.543 ton/hour of the condensation liquid are obtained at a top of the rinsing tower, then enter a dehydrating tower, and next enter a decomposition reactor. In the meantime, 34 kilo/hour of bis(tert-butyl)chromate cyclohexane solution having 3% of chromium are added to the decomposition reactor as a homogeneous catalyst. A stirrer of the decomposition reactor is activated to stir, for uniformly distributing the catalyst into the liquid inside the decomposition reactor and thus catalyzing the peroxide to decompose into cyclohexanol and cyclohexanone. In order to prevent the catalyst from scaling and depositing, in the meantime, 14 kilo/hour of the phosphoric acid octyl ester are added to the decomposition reactor as the scale inhibitor. Under a pressure of 0.03 MPa and at a temperature of 91° C., a homogeneous catalytic decomposition of the peroxide is performed at a residence time of 25 minutes, which results in a decomposition molar conversion rate of 91%, a total molar yield of around 94% and a continuous production cycle of four months. Then, after stalling, the decomposition reactor and correspondent pipelines are cleaned by a NaOH aqueous solution, as well as cyclohexane recycling towers at a subsequent step.

Example 1

The Example 1 of the present invention only differs from the Comparison Example in that an amount of the phosphoric acid octyl ester is cut half to be 7 kilo/hour and 0.4 kilo/hour of 1-hydroxy ethidene-1,1-diphosphonic acid (di)octyl ester is added, without changing other reaction conditions. According to the Example 1 of the present invention, a decomposition molar conversion rate reaches 92%; a total molar yield reaches 94%; and a continuous production cycle lasts for six months.

Example 2

The Example 2 of the present invention only differs from the Comparison Example in that the amount of the phosphoric acid octyl ester as the scale inhibitor is completely stopped and wholly replaced by 1 kilo/hour of 1-hydroxy ethidene-1,1-diphosphonic acid (di)octyl ester, without changing other reaction conditions. According to the Example 2 of the present invention, a decomposition molar conversion rate reaches 93%; a total molar yield reaches 94%; and a continuous production cycle lasts for one year.

What is claimed is:

1. A process for preparing cyclohexanol and cyclohexanone from cyclohexane, comprising steps of:
    (1) non-catalyticly oxidizing cyclohexane with molecular oxygen to obtain an oxidized mixture liquid containing cyclohexyl hydroperoxide (CHHP) as a main product;
    (2) performing a homogenous catalytic decomposition with an oil-soluble transitional metal compound which serves as a catalyst to decompose the CHHP into cyclohexanol and cyclohexanone; and
    (3) rectifying to obtain products of the cyclohexanol and the cyclohexanone; wherein
    the step (2) further comprises a step of serving as a scale inhibitor by 1-hydroxy ethidene-1,1-diphosphonic acid dioctyl ester, or a combination of 1-hydroxy ethidene-1,1-diphosphonic acid dioctyl ester and phosphoric acid octyl ester, wherein
    for the step of "serving as the scale inhibitor by 1-hydroxy ethidene-1,1-diphosphonic acid dioctyl ester", a weight ratio of the 1-hydroxy ethidene-1,1-diphosphonic acid dioctyl ester to transitional metal ions of the transitional metal compound is 1:0.8~1.2; for the step of "serving as the scale inhibitor by the combination of 1-hydroxy ethidene-1,1-diphosphonic acid dioctyl ester and the phosphoric acid octyl ester", namely a part of the 1-hydroxy ethidene-1,1-diphosphonic acid dioctyl ester is substituted with the phosphoric acid octyl acid for serving as the scale inhibitor, an amount of the scale inhibitor is calculated according to an equation that a descaling capacity of 20 tons of the phosphoric acid octyl ester is equivalent to a descaling capacity of 1 ton of the 1-hydroxy ethidene-1,1-diphosphonic acid dioctyl ester;

wherein the 1-hydroxy ethidene-1,1-diphosphonic acid dioctyl ester has a molecular structural formula of:

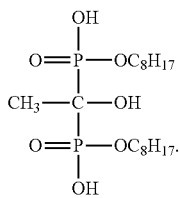

2. The process, as recited in claim 1, wherein the weight ratio of the 1-hydroxy ethidene-1,1-diphosphonic acid dioctyl ester to the transitional metal ions of the catalyst, namely the oil-soluble transitional metal compound, is 1:1.

3. The process, as recited claim 1, wherein when the scale inhibitor is served by the combination of 1 ton of the 1-hydroxy ethidene-1,1-diphosphonic acid dioctyl ester and 20 tons of the phosphoric acid octyl ester, the weight ratio of the amount of the scale inhibitor to the transitional metal ions of the catalyst is 7.4:1.

4. The process, as recited in claim 1, wherein the oil-soluble transitional metal compound is one member selected from a group consisting of cobalt naphthenate, chromium naphthenate, cobalt octoate, chromium octoate and bis(tert-butyl)chromate.

5. The process, as recited in claim 2, wherein the oil-soluble transitional metal compound is one member selected from a group consisting of cobalt naphthenate, chromium naphthenate, cobalt octoate, chromium octoate and bis(tert-butyl)chromate.

6. The process, as recited in claim 3, wherein the oil-soluble transitional metal compound is one member selected from a group consisting of cobalt naphthenate, chromium naphthenate, cobalt octoate, chromium octoate and bis(tert-butyl)chromate.

* * * * *